(12) United States Patent
Bleeker et al.

(10) Patent No.: US 12,094,600 B2
(45) Date of Patent: Sep. 17, 2024

(54) ARTIFICIAL INTELLIGENCE BASED TECHNOLOGIES FOR IMPROVING PATIENT APPOINTMENT SCHEDULING AND INVENTORY MANAGEMENT

(71) Applicant: CDW LLC, Vernon Hills, IL (US)

(72) Inventors: Casey Bleeker, Denver, CO (US); Nathan A. Cartwright, Cincinnati, OH (US)

(73) Assignee: CDW LLC, Vernon Hills, IL (US)

(*) Notice: Subject to any disclaimer, the term of this patent is extended or adjusted under 35 U.S.C. 154(b) by 233 days.

(21) Appl. No.: 17/581,650

(22) Filed: Jan. 21, 2022

(65) Prior Publication Data

US 2023/0238119 A1    Jul. 27, 2023

(51) Int. Cl.
*G16H 40/20* (2018.01)
*G06F 16/2455* (2019.01)
(Continued)

(52) U.S. Cl.
CPC ......... *G16H 40/20* (2018.01); *G06F 16/2455* (2019.01); *G06F 40/30* (2020.01);
(Continued)

(58) Field of Classification Search
CPC ..... G16H 40/20; G06F 16/2455; G06F 40/30; G06Q 10/1095; G10L 15/063;
(Continued)

(56) References Cited

U.S. PATENT DOCUMENTS 8,364,501 B2 * 1/2013 Rana ............... G16H 40/20
705/2
9,536,049 B2 * 1/2017 Brown ............... G10L 15/08
(Continued)

OTHER PUBLICATIONS

Abdalazeim, Procedia Computer Science, 2021, pp. 328-334.*
(Continued)

*Primary Examiner* — Michael I Ezewoko
(74) *Attorney, Agent, or Firm* — MARSHALL, GERSTEIN & BORUN LLP; Randall G. Rueth

(57) ABSTRACT

Artificial intelligence (AI) based technologies for improving patient appointment scheduling and inventory management are disclosed herein. An example method includes receiving, at a server including a natural language processing (NLP) model, an appointment request from a user. The example method further includes initiating, based on the appointment request, a patient appointment data stream including verbal responses from the user regarding an appointment of the user. The example method further includes applying, while simultaneously receiving the patient appointment data stream, the NLP model to the verbal responses from the user to output (i) textual transcriptions and (ii) intent interpretations. The example method further includes querying a scheduling database to determine a matching appointment that satisfies a distance threshold, a date threshold, a service threshold, and an inventory threshold. The example method further includes causing a user device of the user to convey the matching appointment to the user.

20 Claims, 3 Drawing Sheets

(51) Int. Cl.
*G06F 40/30* (2020.01)
*G06Q 10/1093* (2023.01)
*G10L 15/06* (2013.01)
*G10L 15/18* (2013.01)
*G10L 15/22* (2006.01)
*G10L 15/30* (2013.01)
*H04M 1/656* (2006.01)

(52) U.S. Cl.
CPC ........ *G06Q 10/1095* (2013.01); *G10L 15/063* (2013.01); *G10L 15/1815* (2013.01); *G10L 15/22* (2013.01); *G10L 15/30* (2013.01); *H04M 1/656* (2013.01); *G10L 2015/223* (2013.01); *H04M 2201/40* (2013.01)

(58) Field of Classification Search
CPC ..... G10L 15/1815; G10L 15/22; G10L 15/30; G10L 2015/223; H04M 1/656; H04M 2201/40
See application file for complete search history.

(56) References Cited

U.S. PATENT DOCUMENTS

| | | | | |
|---|---|---|---|---|
| 9,824,188 | B2* | 11/2017 | Brown | G06F 3/04886 |
| 10,827,071 | B1* | 11/2020 | Adibi | H04L 67/53 |
| 11,029,918 | B2* | 6/2021 | Brown | G10L 15/08 |
| 11,606,463 | B1* | 3/2023 | Yeracaris | G06Q 30/015 |
| 11,688,509 | B2* | 6/2023 | Hanson | G10L 25/63 |
| | | | | 705/2 |
| 2010/0185465 | A1* | 7/2010 | Rana | G16H 10/20 |
| | | | | 705/2 |
| 2014/0074454 | A1* | 3/2014 | Brown | G10L 15/08 |
| | | | | 704/235 |
| 2014/0337048 | A1* | 11/2014 | Brown | G06F 3/04886 |
| | | | | 705/2 |
| 2017/0329922 | A1* | 11/2017 | Eberting | G16H 40/67 |
| 2018/0039737 | A1* | 2/2018 | Dempers | G06F 21/35 |
| 2018/0068082 | A1* | 3/2018 | Brown | G10L 15/08 |
| 2019/0355450 | A1* | 11/2019 | Altstadter | G16H 40/20 |
| 2020/0227161 | A1* | 7/2020 | Hanson | G06N 3/08 |
| 2020/0258054 | A1* | 8/2020 | Kaufman | G06Q 10/1095 |
| 2021/0004824 | A1* | 1/2021 | Adibi | G06N 5/02 |

OTHER PUBLICATIONS

Ramasubramanian, Springer Science, 2019, pp. 1-700.*
Abdishakur, How to extract locations from text with natural language processing, Medium, Nov. 16, 2020.
International Application No. PCT/US2023/010168, International Search Report and Written Opinion, mailed May 10, 2023.
Written Opinion of the International Preliminary Examining Authority issued in PCT Patent Application No. PCT/US2023/010168 dated Dec. 12, 2023.

* cited by examiner

ARTIFICIAL INTELLIGENCE BASED TECHNOLOGIES FOR IMPROVING PATIENT APPOINTMENT SCHEDULING AND INVENTORY MANAGEMENT

FIELD OF THE DISCLOSURE

The present disclosure is generally directed to technologies for appointment scheduling and inventory management and, more particularly, to artificial intelligence (AI) techniques for improving patient appointment scheduling and inventory management.

BACKGROUND

Today, many businesses rely on customer contact centers to manage conversations between customers (e.g., patients) and customer representatives. In the modern economic environment, cost-effectively serving and retaining customers is of paramount importance, especially as customer retention is generally less expensive than new customer acquisition. Accordingly, the customer contact center is a cornerstone to a successful business strategy.

Customer contact centers handle a large amount of interaction between customers (e.g., patients) and companies, through customer representatives. As the cost of a live agent is substantial, many businesses have shifted towards interactive voice response (IVR) technology and, more recently, virtual agents that can help offload the live agent to a simple, straightforward task to improve the efficiency of the call center. Through IVR, the interaction with the customer may be classified into a series of steps, which are delivered to the customer in an automated manner, such as a pre-recorded script or multiple choice menus on a computer screen. Accordingly, certain information (e.g., the desired medical procedure or medical insurance account number, etc.) can be automatically obtained (e.g., via the telephone, a keypad, and/or a computer keyboard) before passing control to a live agent.

Virtual agents generally provide a greater set of customer interaction capabilities than IVR to more flexibly accommodate customer requests through a contact center without involving a live agent. More particularly, virtual agents may mimic live agents using scripted rules in conjunction with artificial intelligence (AI) (e.g., natural language processing (NLP) and conversational AI) to provide automated service over the phone or on a webpage. Further, virtual agents may utilize machine learning (ML) to learn from past interactions with customers to generally improve their customer service experience over time.

One conventional form of implementing a customer contact center is medical service providers utilizing such platforms to assist with patient intake. Generally, patient intake is a time-consuming process that can occupy valuable medical resources by preventing and/or otherwise reducing the ability of nurses and other trained medical professionals to perform medical procedures. Some medical providers rely on contact centers to alleviate this issue by automatically performing patient intake without the need of a medical staff member. For example, the contact center may provide centralized customer service and support functions for a medical service provider that provides toll-free assistance for patients who need help. In this example, IVR technology may prompt a patient to provide their name, medical insurance account number, and/or other suitable information in order to return an account balance related to a recent procedure the patient received by the medical service provider. However, these conventional contact centers suffer from several problems.

For example, conventional IVR contact centers typically do not include dynamic conversation flows that actively update information relating to multiple service provider locations (also referenced herein as "service locations"). Patients may generally be unaware of medical service providers in their area, and often desire to receive information/suggestions related to nearby medical service providers and the services and availability of those services when deciding to seek medical attention. As mentioned, a typical IVR contact center for a healthcare provider may include a pre-configured set of prompts and acceptable responses from a patient regarding the patient's medical history, information, etc. that may be retrieved from a database associated with a single service provider location (e.g., a particular hospital, a particular private practice office). Accordingly, these typical IVR contact centers do not incorporate data from multiple service provider locations, much less incorporate actively updated data corresponding to the multiple service provider locations, thereby preventing the patient from receiving information regarding any other service provider locations outside the specific provider location associated with the IVR contact center and generally limiting the patient's knowledge and potential for adequate healthcare.

Even virtual agent contact centers typically lack the capability to efficiently handle customer requests that involve complex scheduling accommodations, due to a similar lack of information regarding multiple service provider locations and outdated conversation flows that are difficult and time-consuming to update. Namely, conventional virtual agent contact centers suffer from the same lack of information corresponding to multiple, different service provider locations across a region in order to provide a patient with up-to-date, relevant information regarding an optimal location to address the patient's medical concern(s). For example, both conventional virtual agent contact centers and conventional IVR contact centers are unable to utilize data indicating the availability of medical staff at multiple service provider locations, along with intake data of the user (also referenced herein as a "patient"), in order to determine a suitable appointment for a patient. Thus, conventional contact centers often misdirect patients to erroneous destinations for further intake and/or are simply unable to schedule appointments for patients during the intake process. As a result, conventional contact centers frequently prolong the intake process, delay scheduling of appointments for patients, and correspondingly detrimentally impact the patient's healthcare as they await suitable appointments.

Further, these conventional contact center systems typically lack in-depth information relating to any particular service provider location, such as current inventory, medical equipment (e.g., MRI machine, PET/CT scanner) that may only be located at particular service provider locations, and/or other information that may be critical to a patient's scheduling decision. More specifically, such conventional contact centers may ignore the available inventory of medical supplies and/or other necessary equipment for certain service providers to provide certain services. This lack of inventory information further prevents such conventional contact centers from providing accurate and efficient scheduling for patients at the time of patient intake, as certain service provider locations may be currently unable to provide particular services if the equipment necessary to provide those particular services are unavailable at the certain service provider location. Consequently, conventional contact centers may suggest a patient visit a nearby service provider location that lacks the necessary equipment to perform the service required by the patient, resulting in wasted time and the patient going untreated.

Moreover, such conventional contact centers are especially ineffective for rural and elderly populations, as such individuals are typically unable to receive tele-health services and/or tend to struggle with more modern, web-based platforms. These conventional contact centers typically require access to computing devices that are not prevalent in rural communities, and thereby exclude those individuals from receiving tele-health services. Generally speaking, elderly populations are similarly unable to receive these services using conventional contact centers because the web-based versions of such contact centers often crash and/or otherwise fail in manners that prevent elderly users from easily accessing the services. Consequently, conventional contact centers leave many rural/elderly individuals without viable options to schedule health care services, resulting in a lack of quality and timely health care for a large portion of the population.

Overall, conventional contact centers for automated patient intake provide limited, and in many instances, insufficient information to millions of patients that rely on such systems to receive critical medical care. Correspondingly, a major point of emphasis in the healthcare industry is accurately and efficiently performing patient intake through a contact center, as this poses a substantial challenge for traditional contact centers. Accordingly, there is a need for artificial intelligence (AI) based technologies for improving patient appointment scheduling and inventory management by quickly and seamlessly generating textual transcriptions and textual interpretations of a patient's intake data stream to facilitate consistent and reliable patient intake, scheduling, and inventory management through a contact center.

SUMMARY

The embodiments described herein relate to, inter alia, artificial intelligence (AI) based technologies for improving patient appointment scheduling and inventory management through contact centers. Specifically, the present techniques enable efficient and accurate patient intake by applying a trained natural language processing (NLP) model to verbal responses of a user, generating textual transcriptions and intent interpretations of the verbal responses, and identifying a matching appointment for the user that satisfies distance, date, service, and inventory thresholds based on the textual transcriptions and intent interpretations of the verbal responses. The present techniques differ from traditional patient intake at least in that they streamline the intake process, such that the human resources (e.g., medical staff manually performing/re-performing patient intakes), processing resources, memory resources, and time required to perform patient intake are greatly reduced.

Moreover, the present techniques further improve over conventional techniques because they dramatically increase the accessibility and ease with which traditionally underserved populations (e.g., rural, elderly) may receive timely, relevant healthcare. The present techniques utilize a centralized server approach that actively and dynamically pulls in data corresponding to new service provider locations, as well as updates to previously stored service provider locations, thereby eliminating the need of system administrators managing the contact center to manually update conversation flows of the contact center. In particular, this dynamic updating enables the present techniques to include the most up-to-date information related to medical staff scheduling, inventory, available services, medical equipment, and other relevant information for all service provider locations included in the centralized server for a user, at the time of the user's request, without requiring access to expensive and/or otherwise unavailable tele-health resources. Thus, users of the present techniques have affordable access to accurate, real-time scheduling information and scheduling services that were previously unavailable with conventional techniques.

Of course, it should be understood that the present techniques are applicable to any suitable industry, and that the embodiments described herein reference the healthcare industry only for the purposes of discussion. For example, the automotive industry may utilize the present techniques to provide up-to-date information to customers seeking repairs and/or other maintenance for their automobile. A user may transmit a request to a contact center, and the present techniques may enable the contact center to provide the user with real-time information relating to nearby mechanics, parking locations, auto body shops, and/or any other suitable information.

In an embodiment, the present techniques include an artificial intelligence (AI) based method for improving patient appointment scheduling and inventory management. The method comprises: receiving, at a server including a natural language processing (NLP) model and one or more processors, an appointment request from a user, wherein the NLP model is trained with a plurality of verbal responses regarding appointment scheduling of a plurality of users, and the NLP model is configured to output one or more textual transcriptions and one or more intent interpretations corresponding to the one or more textual transcriptions; initiating, by the one or more processors and based on the appointment request, a patient appointment data stream including verbal responses from the user regarding an appointment of the user; applying, by the one or more processors while simultaneously receiving the patient appointment data stream, the NLP model to the verbal responses from the user to output (i) textual transcriptions corresponding to the verbal responses from the user and (ii) intent interpretations corresponding to the textual transcriptions; querying, by the one or more processors, a scheduling database to determine a matching appointment that satisfies a distance threshold, a date threshold, a service threshold, and an inventory threshold based on the textual transcriptions and the intent interpretations; and causing, by the one or more processors, a user device of the user to convey the matching appointment to the user.

In another embodiment, the present techniques include an artificial intelligence (AI) based system for improving patient appointment scheduling and inventory management. The system comprises: a server including one or more processors and a natural language processing (NLP) model that is configured to receive an appointment request from a user, wherein the NLP model is trained with a plurality of verbal responses regarding appointment scheduling of a plurality of users, and the NLP model is configured to output one or more textual transcriptions and one or more intent interpretations corresponding to the one or more textual transcriptions; and one or more memories, storing instructions thereon that, when executed by the one or more processors, cause the one or more processors to: initiate, based on the appointment request, a patient appointment data stream including verbal responses from the user regarding an appointment of the user; apply, while simultaneously receiving the patient appointment data stream, the NLP model to the verbal responses from the user to output (i) textual transcriptions corresponding to the verbal responses from the user and (ii) intent interpretations corresponding to the textual transcriptions; query a scheduling database to determine a matching appointment that satisfies a distance threshold, a date threshold, a service threshold, and an inventory threshold based on the textual transcriptions and the intent interpretations; and cause a user device of the user to convey the matching appointment to the user.

In yet another embodiment, the present techniques include a tangible machine-readable medium comprising instructions for improving patient appointment scheduling and inventory management that, when executed, cause a machine to at least: receive an appointment request from a user; initiate, based on the appointment request, a patient appointment data stream including verbal responses from the user regarding an appointment of the user; apply, while simultaneously receiving the patient appointment data stream, a natural language processing (NLP) model to the verbal responses from the user to output (i) textual transcriptions corresponding to the verbal responses from the user and (ii) intent interpretations corresponding to the textual transcriptions, wherein the NLP model is trained with a plurality of verbal responses regarding appointment scheduling of a plurality of users, and the NLP model is configured to output one or more textual transcriptions and one or more intent interpretations corresponding to the one or more textual transcriptions; query a scheduling database to determine a matching appointment that satisfies a distance threshold, a date threshold, a service threshold, and an inventory threshold based on the textual transcriptions and the intent interpretations; and cause a user device of the user to convey the matching appointment to the user.

BRIEF DESCRIPTION OF THE DRAWINGS

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

The figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

Exemplary Computing Environment

Figure 1:
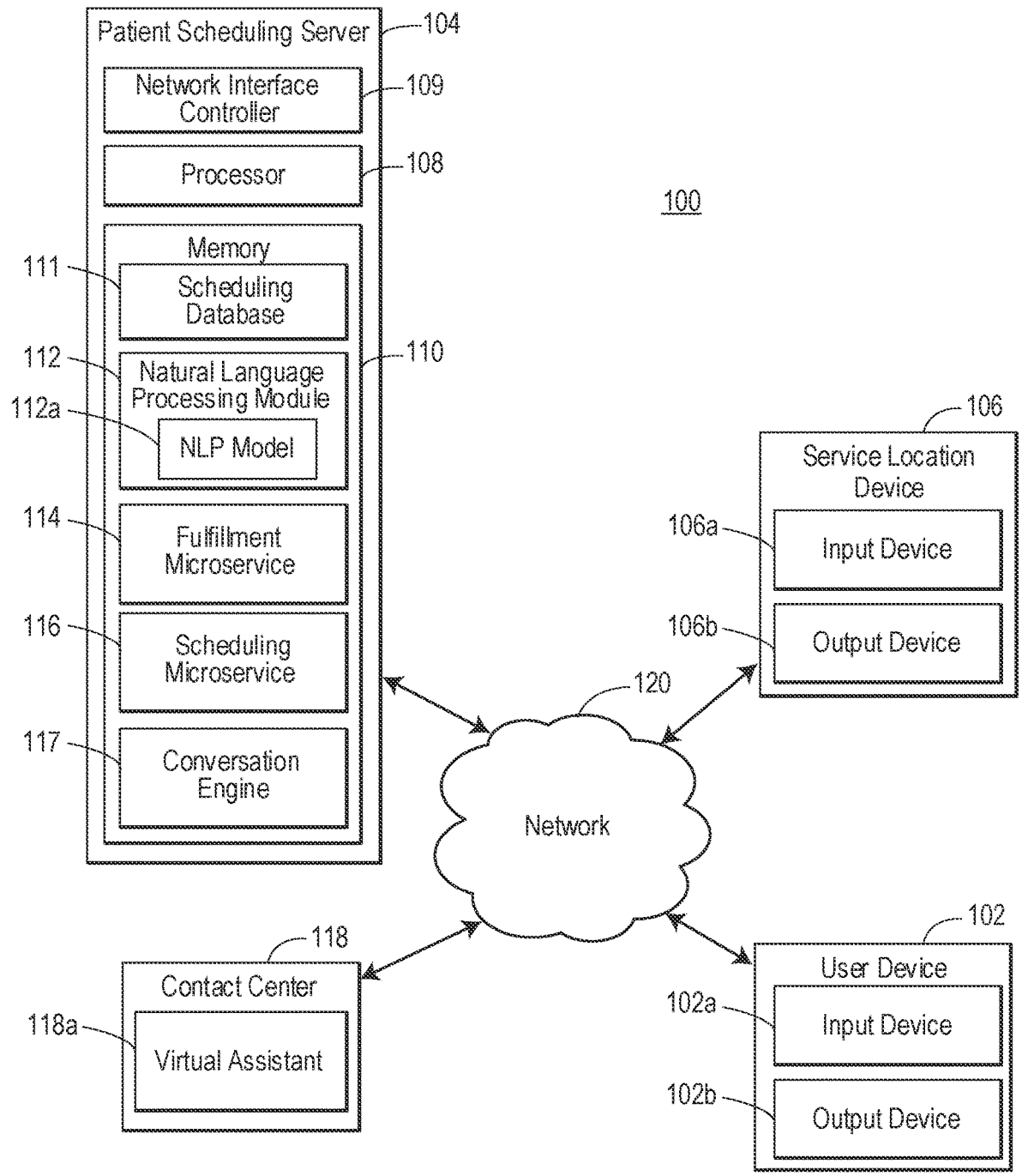
FIG. 1 depicts an exemplary computing environment in which artificial intelligence (AI) based technologies for improving patient appointment scheduling and inventory management may be implemented, in accordance with embodiments described herein.

FIG. 1 depicts an exemplary computing environment 100 which artificial intelligence (AI) based technologies for improving patient appointment scheduling and inventory management may be implemented, according to an embodiment. The environment 100 includes a user device 102, a patient scheduling server 104, a service location device 106, a contact center 118, and a network 120. Some embodiments may include a plurality of user devices 102, a plurality of service location devices 106, a plurality of patient scheduling servers 104, and/or a plurality of contact centers 118.

Generally, the user device 102 may include an input device 102a and an output device 102b. The input device 102a may include any suitable device or devices for receiving input, such as one or more microphone, one or more camera, a hardware keyboard, a hardware mouse, a capacitive touch screen, etc. The output device 102b may include any suitable device for conveying output, such as a hardware speaker, a computer monitor, a touch screen, etc. In some cases, the input device 102a and the output device 102b may be integrated into a single device, such as a touch screen device that accepts user input and displays output.

The service location device 106 may include an input device 106a and an output device 106b. The input device 106a may include any suitable device or devices for receiving input, such as one or more microphone, one or more camera, a hardware keyboard, a hardware mouse, a capacitive touch screen, etc. The output device 106b may include any suitable device for conveying output, such as a hardware speaker, a computer monitor, a touch screen, etc. In some cases, the input device 106a and the output device 106b may be integrated into a single device, such as a touch screen device that accepts user input and displays output. In certain aspects, the service location device 106 may be a healthcare service provider device, and/or any other suitable service provider that may interact with the user (e.g., via the user device 102) based on the patient appointment scheduling performed by executable instructions stored on the patient scheduling server 104.

The service location device 106 may also enable the service provider to provide updates to an information stored in the scheduling database 111 of the patient scheduling server 104. For example, a user of the service location device 106 may desire to update the list of available services at the particular service location corresponding to the service location device 106. The user may utilize the input device 106a to enter/upload information from the service location device 106 to the patient scheduling server 104, where the information may be stored on the scheduling database 111. A user of the service location device 106 may actively provide updates to any suitable information, such as currently available services at the particular location (e.g., vaccinations, surgeries, etc.), schedules of medical professionals certified to perform the currently available services, current medical supply inventory (e.g., vaccines) at the particular service location, medical equipment (e.g., MRI machine, PET/CT scanner) located at the particular service location, and/or other information that may be critical to the user's scheduling decision or combinations thereof. This information may then be uploaded and stored onto the scheduling database for immediate access by the patient scheduling server 104 for any subsequent requests from users.

The patient scheduling server 104 may be an individual server, a group (e.g., cluster) of multiple servers, or another suitable type of computing device or system (e.g., a collection of computing resources). In some embodiments, one or more components of the patient scheduling server 104 may be embodied by one or more virtual instances (e.g., a cloud-based virtualization service). In such cases, one or more patient scheduling server 104 may be included in a remote data center (e.g., a cloud computing environment, a public cloud, a private cloud, etc.). As such, in certain instances, the processing resources (e.g., processor 108), databases (e.g., scheduling database 111), modules (e.g., natural language processing module 112), microservices (e.g., fulfillment microservice 114, scheduling microservice 116), engines (e.g., conversation engine 117), and/or any other stored data/executable instructions may be distributed in various diverse computing environments. Thus, in these instances, any component of the server 104 may run/execute and/or be stored in various computing resources connected by the network 120.

In any event, the patient scheduling server 104 includes a processor 108 and a network interface controller (NIC) 109. The processor 108 may include any suitable number of processors and/or processor types, such as CPUs and one or more graphics processing units (GPUs). Generally, the processor 108 is configured to execute software instructions stored in a memory 110. The memory 110 may include one or more persistent memories (e.g., a hard drive/solid state memory) and stores one or more set of computer executable instructions/modules, including a scheduling database 111, a natural language processing (NLP) module 112, a fulfillment microservice 114, a scheduling microservice 116, and a conversation engine 117.

The NIC 109 may include any suitable network interface controller(s), such as wired/wireless controllers (e.g., Ethernet controllers), and facilitate bidirectional/multiplexed networking over the network 120 between the patient scheduling server 104 and other components of the environment 100 (e.g., user device 102, the contact center 118, the service location device 106, etc.).

Each of the modules stored in memory 110 implement specific functionality. The scheduling database 111 stores up-to-date information related to multiple service locations that is actively updated by users/administrators that have access to the patient scheduling server 104. The scheduling database 111 may include any suitable data corresponding to the multiple service locations, such as, schedules for particular service providers (e.g., physicians, technicians, etc.), available inventory corresponding to particular procedures (e.g., vaccinations), available medical equipment corresponding to particular procedures (e.g., PET/CT machine), and/or any other suitable information or combinations thereof.

The NLP module 112 includes computer-executable instructions for training, deploying, operating, and receiving inferences from an NLP model 112a. In general, the NLP module 112 may train one or more NLP models 112a by establishing a network architecture, or topology, and adding layers that may be associated with one or more activation functions (e.g., a rectified linear unit, softmax, etc.), loss functions and/or optimization functions. Such training may generally be performed using a symbolic method, machine learning (ML) models, and/or any other suitable training method. More generally, the NLP module 122 may train the NLP models 112a to perform two techniques that enable the patient scheduling server 104, the contact center 118, and/or any other suitable device to understand the words spoken by a patient: syntactic analysis and semantic analysis.

Syntactic analysis generally involves analyzing text using basic grammar rules to identify overall sentence structure, how specific words within sentences are organized, and how the words within sentences are related to one another. Syntactic analysis may include one or more sub-tasks, such as tokenization, part of speech (POS) tagging, parsing, lemmatization and stemming, stop-word removal, and/or any other suitable sub-task or combinations thereof. For example, using syntactic analysis, the NLP model 112a may generate the textual transcriptions from the verbal responses from the user as part of the patient appointment data stream.

Semantic analysis generally involves analyzing text in order to understand and/or otherwise capture the meaning of the text. In particular, the NLP model 112a applying semantic analysis may study the meaning of each individual word contained in a textual transcription in a process known as lexical semantics. Using these individual meanings, the NLP model 112a may then examine various combinations of words included in the sentences of the textual transcription to determine one or more contextual meanings of the words. Semantic analysis may include one or more sub-tasks, such as word sense disambiguation, relationship extraction, sentiment analysis, and/or any other suitable sub-tasks or combinations thereof. For example, using semantic analysis, the NLP model 112a may generate the one or more intent interpretations based on the one or more textual transcriptions from the syntactic analysis.

As such, the NLP module 112 may train the one or more NLP models 112a to apply these and/or other NLP techniques using a plurality of verbal responses regarding appointment scheduling of a plurality of users. As a result, the NLP model 112a may be configured to output one or more textual transcriptions and one or more intent interpretations corresponding to the one or more textual transcriptions based on the syntactic analysis and semantic analysis of the patient's verbal responses as part of the patient appointment data stream.

In certain aspects, one or more types of machine learning (ML) may be employed to by the NLP module 112 to train the NLP model(s) 112a. Further, in some aspects, the NLP model(s) 112a may be one or more types of ML models. For example, artificial neural networks, recurrent neural networks, deep learning neural networks, a Bayesian model, and/or any other suitable ML model may be used to train and/or otherwise implement the NLP model(s) 112a. In these aspects, training may be performed by iteratively training the network using labeled training samples.

In instances where the NLP model(s) 112a is an artificial neural network, training of the NLP model(s) 112a may produce byproduct weights, or parameters which may be initialized to random values. The weights may be modified as the network is iteratively trained, by using one of several gradient descent algorithms, to reduce loss and to cause the values output by the network to converge to expected, or "learned", values. In embodiments, a regression neural network may be selected which lacks an activation function, wherein input data may be normalized by mean centering, to determine loss and quantify the accuracy of outputs. Such normalization may use a mean squared error loss function and mean absolute error. The artificial neural network model may be validated and cross-validated using standard techniques such as hold-out, K-fold, etc. In embodiments, multiple artificial neural networks may be separately trained and operated, and/or separately trained and operated in conjunction.

In embodiments, the one or more NLP models 112a may include an artificial neural network having an input layer, one or more hidden layers, and an output layer. Each of the layers in the artificial neural network may include an arbitrary number of neurons. The plurality of layers may chain neurons together linearly and may pass output from one neuron to the next, or may be networked together such that the neurons communicate input and output in a non-linear way. In general, it should be understood that many configurations and/or connections of artificial neural networks are possible. For example, the input layer may correspond to input parameters that are given as full sentences, or that are separated according to word or character (e.g., fixed width) limits. The input layer may correspond to a large number of input parameters (e.g., one million inputs), in some embodiments, and may be analyzed serially or in parallel. Further, various neurons and/or neuron connections within the artificial neural network may be initialized with any number of weights and/or other training parameters. Each of the neurons in the hidden layers may analyze one or more of the input parameters from the input layer, and/or one or more outputs from a previous one or more of the hidden layers, to generate a decision or other output. The output layer may include one or more outputs, each indicating a prediction. In some embodiments and/or scenarios, the output layer includes only a single output.

Generally, both the fulfillment microservice 114 and the scheduling microservice 116 may be part of a library of application programming interfaces (APIs) that are stored in the memory 110, and that are configured to access and otherwise fulfill requests included within the intent interpretations of a user's verbal responses. For example, the fulfillment microservice 114 may receive a request to retrieve an appointment from the scheduling database 111. The fulfillment microservice 114 may include computer-executable instructions that, when executed, cause a computer to access the scheduling microservice 116 in order to obtain the requested appointment. The scheduling microservice 116, in turn, may include computer-executable instructions that, when executed, cause the computer to obtain available appointments for various services provided by various service professionals corresponding to the requested appointment.

To illustrate, the patient scheduling server 104 may receive an appointment request from a user that initiates a patient appointment data stream including verbal responses from the user regarding an appointment of the user. The user may verbally indicate their location (e.g., zip code, address, city, state, etc.) and that they want to visit a doctor to receive a vaccination for a particular disease within the next two weeks. Upon initiating this patient appointment data stream, the patient scheduling server 104 may utilize an NLP model 112a (trained by the NLP module 112) to determine textual transcriptions from the patient appointment data stream along with intent interpretations based on the textual transcriptions to determine where the user is located, and what service the user is requesting. The server 104 may then utilize the fulfillment microservice 114 to transmit a query request to the scheduling microservice 116 indicating that the user requests (1) a vaccination for the particular disease, (2) within the next two weeks, and (3) within X miles of the user's location. The "X" may indicate any suitable number of miles and/or any other suitable distance metric. For example, the patient scheduling server 104 may automatically sort through appointments returned by the scheduling microservice 116 to eliminate any appointments at service locations further than 10 miles from the user's location.

The fulfillment microservice 114 may also transmit a request to a suitable service that may convert the user's location to a suitable format. Continuing the prior example, the fulfillment microservice 114 may transmit a request through a mapping API (e.g., GOOGLE MAPS API) to convert the user's location to global positioning system (GPS) coordinates and/or any other suitable coordinates or combinations thereof. This conversion may enable the patient scheduling server 104, and more particularly, the scheduling microservice 116 to determine the distance from the user's current location to each service location which has an otherwise acceptable appointment available. For example, assume that a first service location and a second service location have available inventory of the user's requested vaccine, and that both service locations have service professionals available to administer the vaccine within the next 2 weeks. In this example, further assume that the first service location is within 10 miles of the user's location, and that the second service location is further than 10 miles from the user's location. The scheduling microservice 116 may determine that the first service location does have a matching appointment because it satisfies all of the requirements (e.g., satisfies all thresholds), and that the second service location does not have a matching appointment simply because it is further than 10 miles from the user's location.

In any event, the scheduling microservice 116 may query the scheduling database 111 to identify suitable appointments based on the criteria transmitted by the fulfillment microservice 114 as part of the query request. More specifically, the scheduling microservice 116 may examine the updated schedules and inventory of each service location to determine which service locations satisfy all requirements determined from the textual transcriptions and corresponding intent interpretations. In the prior example, the scheduling microservice 116 may query the scheduling database 111 to determine a service location that has (1) vaccination services for the particular disease, (2) available inventory of a vaccine for the particular disease, (3) a service professional available to administer the vaccination at a suitable time (e.g., during the next two weeks), and (4) is within 10 miles of the user's location.

More generally, the scheduling microservice 116 and/or the fulfillment microservice 114 may access the scheduling database 111 and/or any other suitable database via a socket, a persistent network connection, or any other suitable means. In some cases, the scheduling database 111 may reside entirely in the memory 110 (e.g., an in-memory database). The microservices 114, 116 may load/retrieve one or more databases/tables into the in-memory database.

The conversation engine 117 may generally be an artificial intelligence (AI) trained conversational algorithm that is configured to interact with a user that is accessing the contact center 118. When a user calls and/or otherwise accesses the contact center 118 (e.g., online chat, social media, text messaging, etc.), the user's verbal inputs/responses may be analyzed by the NLP model 112a to generate textual transcriptions and intent interpretations. The conversation engine 117 may receive the textual transcriptions and/or the intent interpretations from the NLP model 112a to generate subsequent responses that are transmitted and displayed to the user (e.g., through the output device 102b).

As an example, a user may utilize the user device 102 to call in to the contact center 118, and the user may proceed to verbally communicate their requests through the input device 102a (e.g., a microphone of the phone) for an appointment to receive a vaccination. These verbal inputs are routed from the contact center 118 to the NLP model 112a through the patient appointment data stream, where the verbal inputs are analyzed to generate textual transcriptions and intent interpretations. The textual transcriptions and/or the intent interpretations are forwarded to the conversation engine 117, which determines a subsequent response that may include asking the user to specify their location, so that the server 104 may retrieve service provider locations close to the user that offer the vaccination. The conversation engine 117 may repeatedly perform this response generation until the user terminates the appointment data stream (e.g., hangs up the phone, disconnects from the website, etc.) and/or until the user receives and confirms a matching appointment that satisfies their requests.

The contact center 118 may generally moderate communications between the user device 102 and the patient scheduling server 104. When a user calls and/or otherwise accesses the contact center 118 (e.g., online chat, social media, text messaging, etc.), the contact center 118 receives the inbound call from the user, and determines how to appropriately route and/or otherwise handle the user's call. The contact center 118 makes this determination using a virtual assistant 118a, which may interact with the user in conjunction with the NLP model 112a and conversation engine 118a. In particular, the virtual assistant 118a may transmit each user input (e.g., voice input, keyboard input, etc.) to the NLP model 112a for textual transcription and/or intent interpretation, and the virtual assistant 118a may display each response generated by the conversation engine 117 and/or the matching appointment on the output device 102b to the user. As such, the virtual assistant 118a may convey the responses from the patient scheduling server 104 to enable the user to determine how to proceed.

The network 120 may be a single communication network, or may include multiple communication networks of one or more types (e.g., one or more wired and/or wireless local area networks (LANs), and/or one or more wired and/or wireless wide area networks (WANs) such as the Internet). The network 120 may enable bidirectional communication between the user device 102, the patient scheduling server 104, the contact center 118, and the service location device 106, or between multiple recipient entity devices 106, for example.

Exemplary Workflow

Figure 2:
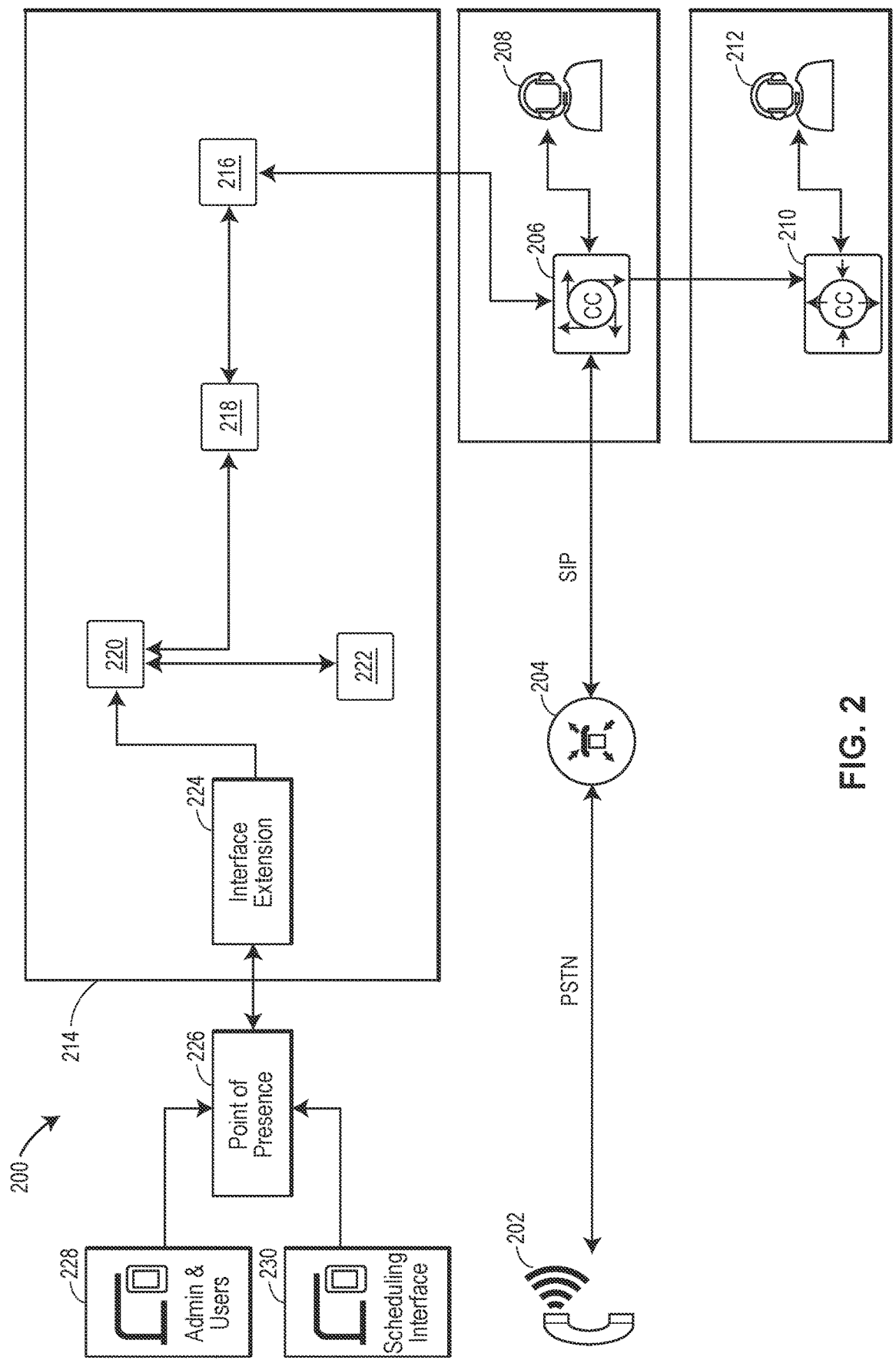
FIG. 2 depicts an exemplary workflow in which artificial intelligence (AI) based technologies for improving patient appointment scheduling and inventory management may be implemented, in accordance with embodiments described herein.

FIG. 2 depicts an exemplary workflow 200 in which artificial intelligence (AI) based technologies for improving patient appointment scheduling and inventory management may be implemented, in accordance with embodiments described herein. Generally speaking, the exemplary workflow 200 includes similar components from the exemplary computing environment 100, and indicates how these similar components may communicate with one another in order to provide improved patient appointment scheduling and inventory management. As part of the exemplary workflow 200, a patient may initiate a patient appointment data stream, which may be handled by the virtual assistant 202 and hosted by the contact center 206. In certain embodiments, the virtual assistant 202 is an interactive voice response (IVR) system that provides verbal responses to the inputs provided by the patient. Of course, in these embodiments, the patient may contact the contact center 206 by calling a particular number using a telephone (e.g., user device 102), such that the virtual assistant 202 may provide the verbal responses through a microphone of the telephone (e.g., output device 102b).

It should be appreciated that the patient's communication with the contact center 206 is referenced herein as a telephone call for ease of discussion only. For example, the patient may initiate a patient appointment data stream using any suitable communication method, such as telephone, through a computer, smart phone/device, and such patient appointment data streams may include audio, video, and/or any other suitable data and may include any other suitable manner of communication or combinations thereof.

When the patient's call is initially received, the call may be transferred through to the contact center 206 by any suitable routing interface, such as a carrier trunking 204. Generally, the carrier trunking 204 may provide access to the contact center for multiple patients simultaneously by sharing a set of circuits, carriers, channels, frequencies, and/or in any other suitable manner such that the individual circuits/channels for each patient are not required. For example, the patient's call may be transmitted to the carrier trunking 204 using a public switched telephone network (PSTN), and the carrier trunking 204 may connect the patient's call to the contact center 206 using a session initiation protocol (SIP) in order to initiate, maintain, and eventually terminate the patient appointment data stream.

In any event, when the patient's call reaches the contact center 206, the call may be routed to the conversational AI 216 (e.g., the conversation engine 117) for processing of the patient's call. For example, the conversational AI 216 may complete an automated patient intake by implementing a natural language processing (NLP) model (e.g., NLP model 112a) to generate textual transcriptions of the patient's verbal responses/inputs and/or intent interpretations based on the textual transcriptions. The conversational AI 216 may also generate responses to each of the patient's verbal responses/inputs, and may transmit those responses back to the virtual assistant 202 for conveying (e.g., verbal communication through the microphone of the telephone) to the patient as part of the conversation that constitutes the patient intake. As the conversational AI 216 receives inputs from the patient, and the NLP model generates the textual transcriptions and/or intent interpretations, the conversational AI 216 may determine that one or more actions should take place. Namely, the conversational AI 216 may utilize the intent interpretations to determine that scheduling/appointment data should be obtained, that a live agent should be contacted, and/or any other suitable action or combinations thereof.

As an example, the conversational AI 216 may determine that a live agent is required. The conversational AI 216 may transmit a signal to the contact center 206 in order to transfer the patient's call from the conversational AI 216 to a live agent 208. In this example, the conversational AI 216 may also transfer any/all patient intake data obtained by the conversational AI 216, along with any scheduling/appointment data obtained by the microservices (218, 220), to the live agent 208 to assist the live agent 208 in quickly and efficiently assisting the patient. In certain instances, the conversational AI 216 may determine that the patient may require assistance from a particular live agent with specific expertise, and may transfer the patient's call to an escalation instance 210 of the contact center 206, where the patient may be transferred to a specialist agent 212. Similar to transferring the patient to the live agent 208, the conversational AI 216 may also transfer any/all patient intake data obtained by the conversational AI 216, along with any scheduling/appointment data obtained by the microservices (218, 220), to the specialist agent 212 to assist the specialist agent 212 in quickly and efficiently assisting the patient.

As an additional example, the conversational AI 216 may utilize the intent interpretations to determine that scheduling/appointment data should be obtained, and may accordingly transmit a signal to the microservice hub 218 in order to obtain the scheduling/appointment data. To illustrate, a patient may request an appointment for a vaccination against COVID-19 within one week of the current date, and the user may also specify their current location. The conversational AI 216 may receive textual transcriptions of this information from the NL model, along with intent interpretations corresponding to this information, and may determine that the fulfillment microservice (e.g., fulfillment microservice 114) should submit a query request to the scheduling microservice (e.g., scheduling microservice 116) to retrieve the corresponding scheduling/appointment data. Accordingly, the conversational AI 216 may transmit the signal to the microservice hub 218, which may include the fulfillment microservice and the scheduling microservice, in order to retrieve the corresponding scheduling/appointment data.

The microservice hub 218 may receive the signal from the conversational AI 216, and may proceed to query the scheduling database 220 (e.g., scheduling database 111) in order to retrieve the scheduling/appointment data relevant to the patient's inputs, as determined by the textual transcriptions and intent interpretations. As previously mentioned, the scheduling database 220 may include actively updated scheduling data from multiple service provider locations, such that a patient calling to request an appointment may receive the most up-to-date information when making their decision. Continuing the prior example, the scheduling microservice may retrieve scheduling information from the scheduling database indicating all locations that offer COVID-19 vaccinations, as well as an updated regulatory listing including a COVID-19 vaccination prioritization schedule. The vaccination prioritization schedule may generally include priority listings of patients who are eligible to receive vaccinations, and may list/sort the patients by any suitable metric, such as age, weight, pre-existing conditions, and/or any other criteria or combination thereof. The vaccination prioritization schedule may also include listings related to the timetables for receiving vaccination doses, boosters, etc. Thus, the scheduling microservice may first check to ensure that the patient is eligible to receive the COVID-19 vaccination based on the patient's stated age (or other relevant criteria) compared to the eligible ages indicated in the COVID-19 vaccination prioritization schedule.

Further, the scheduling microservice may check the textual transcriptions and/or intent interpretations to determine which dose of the COVID-19 vaccination (e.g., first dose, second dose, booster, etc.) the patient is requesting. If the patient is requesting a subsequent dose of the COVID-19 vaccination, then the scheduling service may also check the textual transcriptions and/or intent interpretations to determine when the patient received their prior dose, so that the scheduling microservice may determine when the patient should optimally receive the subsequent dose. The scheduling microservice may also cross-check this determination with the vaccination prioritization schedule to ensure that the patient is eligible to receive the subsequent dose at the prescribed time. Each appointment for a COVID-19 vaccination in the scheduling database 220 may include flags and/or other identifiers indicating what dose of the vaccination to which the appointment corresponds. For example, a first appointment at a first service provider location may include a flag indicating that the first appointment is reserved for COVID-19 vaccinations, and may further indicate that the first appointment is intended for second doses. Additionally, a second appointment at the first service provider location may include a flag indicating that the second appointment is reserved for COVID-19 vaccinations, and may further indicate that the second appointment is intended for booster shots, but may be allocated for first/second doses in the event that no booster shot is scheduled at the time of the second appointment by a cut-off date/time.

Additionally, or alternatively, the flags may indicate a particular manufacturer of a vaccine. As an example, a first appointment at a first service provider location may include a flag indicating that the first appointment is reserved for COVID-19 vaccinations, and may further indicate that the vaccine administered at the first appointment is manufactured by pharmaceutical company A. Additionally, a second appointment at the first service provider location may include a flag indicating that the second appointment is reserved for COVID-19 vaccinations, and may further indicate that the vaccine administered at the second appointment manufactured by pharmaceutical company B. In this manner, patient's may specify a vaccine manufacturer to more effectively manage their vaccinations by maintaining a single manufacturer throughout a multiple dose vaccination, and/or receiving vaccines made by multiple different manufacturers (e.g., first/second dose by company A, booster by company B).

In any event, when the scheduling microservice has validated that the patient is eligible to receive the COVID-19 vaccination, the microservice may sort through service provider location data stored on the scheduling database 220 to identify appointments that match the patient's criteria, included in the textual transcriptions. For example, the scheduling microservice may examine the scheduling data uploaded by service provider location A to the scheduling database 220 to determine that the service provider location A offers first doses of a vaccine manufactured by pharmaceutical company A at the date/time specified by the user and validated based on the COVID-19 vaccination prioritization schedule. The scheduling microservice may also examine the scheduling data uploaded by service provider location B to the scheduling database 220 to determine that the service provider location B offers first doses of the vaccine manufactured by pharmaceutical company A at the date/time specified by the user and validated based on the COVID-19 vaccination prioritization schedule. In this case, the scheduling microservice may analyze the locations of service provider locations A and B to determine which one is closer to the patient. The scheduling microservice may determine that the service provider location A is closer to the patient's current location, and as a result, the scheduling microservice may return a matching appointment at service provider location A for the patient to consider.

More specifically, the scheduling microservice may determine which of service provider locations A and B is closer to the patient by submitting a request to the fulfillment microservice to calculate distances between the service provider locations A and B and the patient's current location. As previously mentioned, the fulfillment microservice may receive the request, and may utilize a mapping API to convert the patient's current location to global positioning system (GPS) coordinates and/or any other suitable coordinates or combinations thereof and/or to calculate the distances between the patient's current location and the service provider locations A and B. This conversion and calculation may enable the scheduling microservice to determine which of service provider location A and B is closer to the patient's current location. Accordingly, if the scheduling microservice receives calculations (or calculates) that the distance between the patient's current location and service provider location A is 3 miles while the distance between the patient's current location and service provider location B is 7 miles, then the scheduling microservice may determine that the appointment at service provider location A is the matching appointment.

Also, the scheduling microservice may check relevant thresholds in order to determine the matching appointment. Namely, as previously mentioned, the scheduling microservice may analyze the data in the scheduling database 220 to determine whether or not appointments at any particular service provider location satisfies a distance threshold, a date threshold, a service threshold, and/or an inventory threshold based on the textual transcriptions and the intent interpretations. The distance threshold may correspond to a maximum distance the service provider location may be from the patient's current location in order for the scheduling microservice to recommend an appointment associated with the service provider location to the patient as a matching appointment. The date threshold may correspond to a range of dates around a date specified by the patient during which an appointment at a particular service provider location may be considered by the scheduling microservice as a matching appointment. For example, the date threshold may be one day, such that if a patient requests a COVID-19 vaccination one week from the current date, the scheduling microservice may only consider appointments at service provider locations that are within one day (e.g., before, on, or after) of the one week date from the current date as a matching appointment.

Further, the service threshold may correspond to a particular service the patient specifies during the call. If the scheduling microservice identifies an appointment for a service that differs from the service threshold, then the appointment may not be considered as a matching appointment. For example, if the patient desires a booster shot COVID-19 vaccination, and a particular appointment includes a flag indicating that the appointment is intended for a surgery, then the appointment may not be considered as a matching appointment. The inventory threshold may correspond to the available required resources in order to perform the patient's specified service. For example, an inventory threshold for a COVID-19 vaccination may be a service professional qualified to administer the vaccine, as well as available inventory of the particular vaccine specified by the patient. The patient may desire a first dose of the COVID-19 vaccination manufactured by pharmaceutical company A, so the scheduling microservice may only consider appointments including flags indicating that the appointment is intended for a first dose of the COVID-19 vaccination, and that the particular vaccination administered is manufactured by pharmaceutical company A as matching appointments.

With continuing reference to FIG. 2, the scheduling microservice may determine a matching appointment, the patient may review the matching appointment, and may decide to accept or reject the matching appointment. If the patient rejects the matching appointment, the conversational AI 216 may prompt the patient for further input and/or the scheduling microservice may provide a subsequent matching appointment for the patient's consideration. However, if the patient accepts the matching appointment, the scheduling microservice may update the trigger module 222 with the accepted appointment and the patient's information. The trigger module 222 may generally store schedules/calendars corresponding to each service provider location and may create/update these schedules/calendars when a new service provider location is added to the scheduling database 220. In this manner, the trigger module 222 may track logistics corresponding to each service provider location. For example, as a result of tracking the updated schedules for a particular service provider location, the trigger module 222 may track the available inventory of a particular medical supply/equipment necessary to perform a particular medical service. Further in this example, the trigger module 222 may track the available supply of COVID-19 vaccines at a particular service provider location based on the stated inventory of COVID-19 vaccines compared to the number of scheduled COVID-19 vaccinations.

As another example, the trigger module 222 may track whether or not a particular service provider location has sufficient medical professionals to accommodate additional appointments for a particular medical service. If the particular service provider location has a medical professional take a vacation, the medical professional's schedule may be updated into the scheduling database 220 and the trigger module 222 may determine that the particular service provider location may be unable to accommodate additional appointments for a particular medical service during the medical professional's vacation that only the medical professional was qualified to perform.

Thus, in general, the trigger module 222 may enable the example workflow 200 to actively track the overall inventory (e.g., supplies, qualified professionals, location capacity, etc.) that is necessary to perform the particular services offered by the particular service provider location. If the trigger module 222 identifies any potential interruption to the scheduling of a particular service provider location, the trigger module 222 (and/or any other suitable component described herein) may transmit a notification to the service provider location (e.g., by service location device 106) notifying the service provider location of the potential interruption. This notification capability may allow service provider locations to intelligently and proactively manage their inventory in order to avoid disruptions to their scheduling and available appointments due to unforeseen shortages of inventory.

For example, the trigger module 222 may transmit a notification to a first service provider location indicating that the first service provider location is running low on available COVID-19 vaccinations, based on the stored inventory of such vaccinations in the scheduling database 220 and the number of COVID-19 vaccinations scheduled to be administered based on the appointments included on the calendar associated with the first service provider. Accordingly, the first service provider may read the notification and order additional COVID-19 vaccines to meet the expected demand for such vaccines without experiencing any disruptions to their vaccination administration. Alternatively, the first service provider location may read the notification, and may reach out to a second service provider location that is also connected to the example workflow 200 (e.g., through a service location device 106) to request vaccines from their inventory in order to respond to an immediate need for additional vaccines.

The scheduling database 220 may be connected to the service provider locations through an interface extension 224 that moderates communications between the scheduling database 220, trigger module 222, and the microservice hub 218 and the point of presence (POP) 226. The POP 226 may represent the point at which peering occurs between the service provider locations and a cloud platform 214. For example, the administrators and users 228 from the service provider locations and a scheduling interface 230 may enable the service provider locations to communicate with the cloud platform 214 to upload any of the scheduling/ appointment data that may be stored on the scheduling database 220, as described herein. The POP 226 may also transmit schedule/calendar updates, inventory notifications, and/or other suitable communications from the cloud platform 214 to the administrators and users 228 (e.g., using individual devices connected to the network) and the scheduling interface 230 (e.g., the service location device) for viewing and storage at and/or otherwise corresponding to a service provider location.

In certain instances, the POP 226 may be part of a GOOGLE cloud-based platform (e.g., the cloud platform 214) and may be a GOOGLE EDGE POP. Of course, the POP 226 may be of any suitable configuration from any suitable developer or combinations thereof. Additionally, the conversational AI 216, microservice hub 218, the scheduling database 220, the trigger module 222, and the interface extension 224 may generally be included as part of the cloud platform 214 that stores resources that are accessible by each user (e.g., "tenant") of the cloud platform 214. Of course, it should be understood that the cloud platform 214 may be any suitable computing resource that includes a POP/peering location. For example, in certain instances, the cloud platform 214 may be a GOOGLE cloud platform, a public cloud platform, a private cloud platform, an internet accessible datacenter/colocation facility, and/or any other suitable platform.

Exemplary Method

Figure 3:
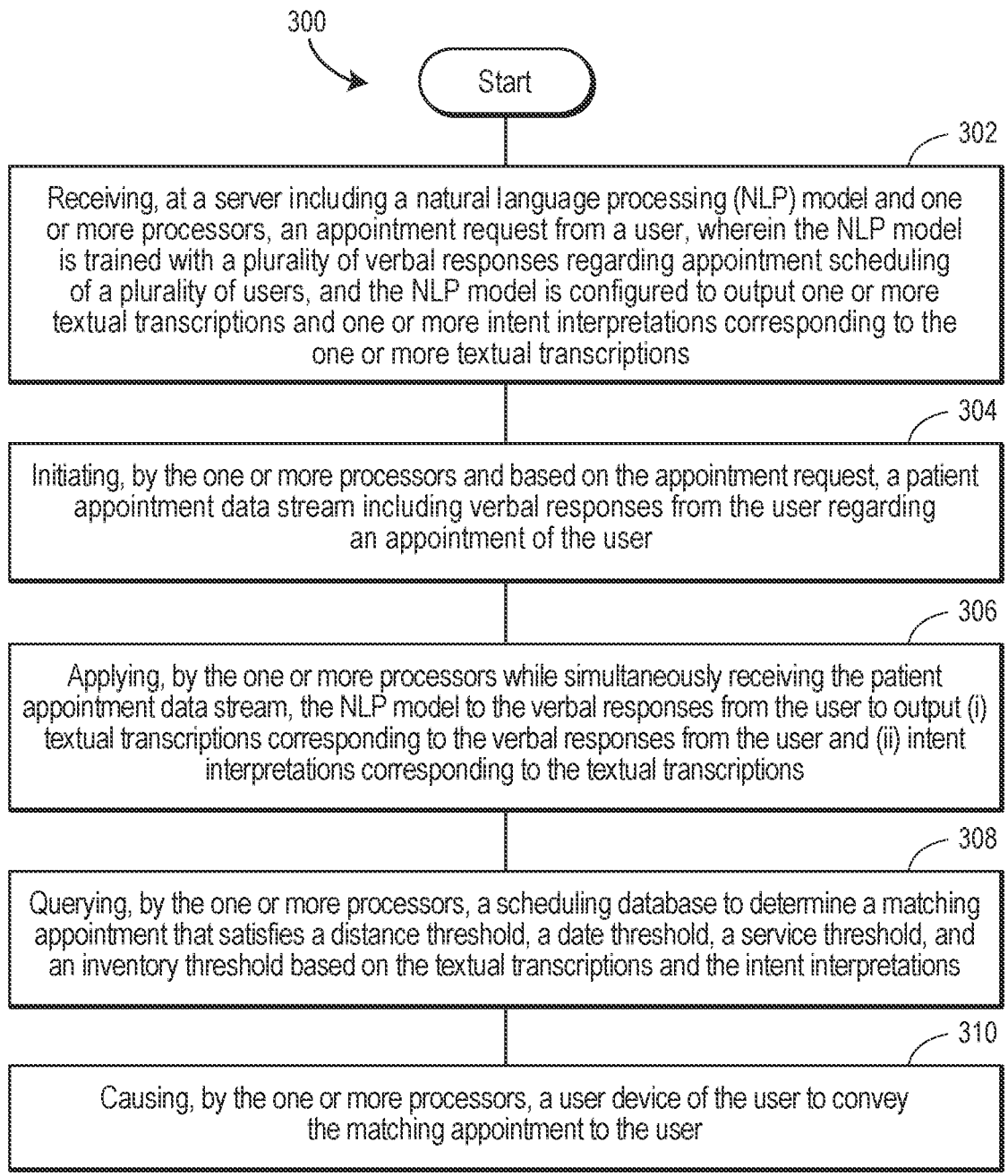
FIG. 3 is a flow diagram of an example AI based method for improving patient appointment scheduling and inventory management, in accordance with embodiments described herein.

FIG. 3 is a flow diagram of an example AI based method 300 for improving patient appointment scheduling and inventory management, in accordance with embodiments described herein. At least portions of the method 300 may be performed by one or more processors (e.g., one or more processors 108) utilizing the embodiments of the patient scheduling server 104, the contact center 118 of FIG. 1, for example, or by other suitable modules or systems. In some aspects, the method 300 may include additional or alternate steps other than those described herein.

The example method 300 begins (block 302) by receiving, at a server including a natural language processing (NLP) model (e.g., NLP model 112*a*) and one or more processors, an appointment request from a user. The NLP model may be trained with a plurality of verbal responses regarding appointment scheduling of a plurality of users, and the NLP model may be configured to output one or more textual transcriptions and one or more intent interpretations corresponding to the one or more textual transcriptions. The example method 300 may also include initiating, by the one or more processors and based on the appointment request, a patient appointment data stream including verbal responses from the user regarding an appointment of the user (block 304).

When the patient appointment data stream is initiated, the example method 300 may further include applying, by the one or more processors while simultaneously receiving the patient appointment data stream, the NLP model to the verbal responses from the user to output (i) textual transcriptions corresponding to the verbal responses from the user and (ii) intent interpretations corresponding to the textual transcriptions (block 306). For example, the one or more textual transcriptions may correspond to the verbal responses spoken by the user during the patient appointment data stream, such as "I would like an appointment for a COVID-19 vaccine one week from now." The NLP model may also generate intent interpretations from this textual transcription, that generally correspond to the meaning of the user's verbal responses and actions the systems described herein may take to fulfill these intents. For example, intent interpretations of the user's prior textual transcription may indicate that the user desires scheduling/appointment information for a COVID-19 vaccination, and that the scheduling/appointment information must indicate that the appointment is exactly (or within a date threshold) one week from the current date.

In certain instances, the textual transcription includes a user-specified service, and the service threshold corresponds to the user-specified service. For example, the user-specified service may be receiving a COVID-19 vaccination, so the service threshold may cause the scheduling microservice to not categorize any appointment that is not for a COVID-19 vaccination as a matching appointment.

The example method 300 may also include querying, by the one or more processors, a scheduling database to determine a matching appointment that satisfies a distance threshold, a date threshold, a service threshold, and an inventory threshold based on the textual transcriptions and the intent interpretations (block 308). Generally, the scheduling database stores service location data corresponding to a plurality of service locations, and the service location data includes the scheduling/appointment data described herein.

In certain instances, the example method 300 may include receiving, at the server (e.g., patient scheduling server 104), new service location data corresponding to a new service location that includes a new service location address. In these instances, the example method 300 may further includes automatically storing, by the server, the new service location data into the scheduling database; receiving a subsequent appointment request from a different user; and querying the scheduling database to determine a subsequent matching appointment. Thus, when the subsequent appointment request from the different user is received, the scheduling database may include and have access to the new service location data, thereby enabling the different user to potentially schedule an appointment at the new service location.

In certain instances, the example method 300 further includes transmitting, by a fulfillment microservice (e.g., fulfillment microservice 114), a query request to a scheduling microservice (e.g., scheduling microservice 116). Further in these instances, and responsive to receiving the query request, the example method 300 may include querying, by the scheduling microservice, the scheduling database to determine the matching appointment.

In some instances, the example method 300 further includes determining, by the one or more processors, a location of the user based on the textual transcriptions. Additionally, the example method 300 may include converting, by the one or more processors, the location of the user to a coordinate value, and converting a respective service location address for each respective service location to a respective coordinate value. Thereafter, the example method 300 may include calculating, by the one or more processors, a respective service location distance from the location of the user for each respective service location of the plurality of service locations. The example method 300 may also include determining, by the one or more processors, a sorted list of service locations based on the respective service location distance for each respective service location of the plurality of service locations; and selecting, by the one or more processors, the matching appointment from the sorted list based on a subset of service locations on the sorted list that satisfy the distance threshold. In these instances, the distance threshold may correspond to a maximum distance value from the location of the user which will enable the scheduling microservice to categorize an appointment as a matching appointment. If a particular service location exceeds the distance threshold, then the scheduling microservice may not categorize the corresponding appointments from the particular service location as a matching appointment.

In certain instances, the scheduling database comprises scheduling data corresponding to a plurality of service locations, wherein the scheduling data corresponding to each service location includes a schedule calendar and an inventory listing. In these instances, the example method 300 may further include comparing, by the one or more processors, the schedule calendar and the inventory listing for each respective service location in the plurality of service locations to the date threshold and the inventory threshold. The example method 300 may also include determining, by the one or more processors, the matching appointment based on a first respective service location that satisfies the distance threshold, the service threshold, the date threshold, and the inventory threshold.

In some instances, the inventory threshold includes a supply inventory threshold and a medical staff inventory threshold. For example, and as previously mentioned, the inventory threshold may include a supply inventory threshold corresponding to a level of available supplies, below which, the trigger module (e.g., trigger module 222) may generate and transmit a notification for the service provider location in order to notify the service provider location that they should order and/or otherwise acquire more inventory of a particular supply (e.g., vaccinations). The medical staff inventory threshold may correspond to a number of available time slots on medical staff calendars, below which, the trigger module may generate and transmit a notification for the service provider location in order to notify the service provider location that they should review their medical staff schedules in order to potentially create additional available appointments, hire additional medical staff, remove currently available appointments, and/or any other suitable actions or combinations thereof.

In certain instances, the scheduling database comprises a regulatory guidance database that includes a prioritization schedule corresponding to one or more services (e.g., regulatory guidelines/timetables/prioritization schedules for COVID-19 vaccinations).

The example method 300 may also include causing, by the one or more processors, a user device of the user to convey the matching appointment to the user (block 310). For example, the user device may be a telephone, and the matching appointment may be conveyed to the user through a verbal communication transmitted through a speaker of the telephone (e.g., output device 102*b* of the user device 102). Of course, the user device may convey the matching appointment to the user in any suitable manner, such as visually on a display screen or user interface, audibly through a microphone, and/or any other suitable manner or combinations thereof.

Aspects of the Disclosure

1. An artificial intelligence (AI) based method for improving patient appointment scheduling and inventory management, the method comprising: receiving, at a server including a natural language processing (NLP) model and one or more processors, an appointment request from a user, wherein the NLP model is trained with a plurality of verbal responses regarding appointment scheduling of a plurality of users, and the NLP model is configured to output one or more textual transcriptions and one or more intent interpretations corresponding to the one or more textual transcriptions; initiating, by the one or more processors and based on the appointment request, a patient appointment data stream including verbal responses from the user regarding an appointment of the user; applying, by the one or more processors while simultaneously receiving the patient appointment data stream, the NLP model to the verbal responses from the user to output (i) textual transcriptions corresponding to the verbal responses from the user and (ii) intent interpretations corresponding to the textual transcriptions; querying, by the one or more processors, a scheduling database to determine a matching appointment that satisfies a distance threshold, a date threshold, a service threshold, and an inventory threshold based on the textual transcriptions and the intent interpretations; and causing, by the one or more processors, a user device of the user to convey the matching appointment to the user.

2. The AI based method of aspect 1, wherein the scheduling database stores service location data corresponding to a plurality of service locations, and the method further comprises: receiving, at the server, new service location data corresponding to a new service location that includes a new service location address; automatically storing, by the server, the new service location data into the scheduling database; receiving, at the server, a subsequent appointment request from a different user; and querying, by the one or more processors, the scheduling database to determine a subsequent matching appointment, wherein the scheduling database includes the new service location data.

3. The AI based method of any one of aspects 1-2, wherein querying the scheduling database further comprises: transmitting, by a fulfillment microservice, a query request to a scheduling microservice; and responsive to receiving the query request, querying, by the scheduling microservice, the scheduling database to determine the matching appointment.

4. The AI based method of any of aspects 1-3, wherein the scheduling database stores service location data corresponding to a plurality of service locations, and the method further comprises: determining, by the one or more processors, a location of the user based on the textual transcriptions; converting, by the one or more processors, the location of the user to a coordinate value; converting, by the one or more processors, a respective service location address for each respective service location to a respective coordinate value; calculating, by the one or more processors, a respective service location distance from the location of the user for each respective service location of the plurality of service locations; determining, by the one or more processors, a sorted list of service locations based on the respective service location distance for each respective service location of the plurality of service locations; and selecting, by the one or more processors, the matching appointment from the sorted list based on a subset of service locations on the sorted list that satisfy the distance threshold, wherein the distance threshold corresponds to a maximum distance value from the location of the user.

5. The AI based method of any one of aspects 1-4, wherein the scheduling database comprises scheduling data corresponding to a plurality of service locations, wherein the scheduling data corresponding to each service location includes a schedule calendar and an inventory listing.

6. The AI based method of aspect 5, further comprising: comparing, by the one or more processors, the schedule calendar and the inventory listing for each respective service location in the plurality of service locations to the date threshold and the inventory threshold; and determining, by the one or more processors, the matching appointment based on a first respective service location that satisfies the distance threshold, the service threshold, the date threshold, and the inventory threshold.

7. The AI based method of any of aspects 1-6, wherein the textual transcription includes a user-specified service, and the service threshold corresponds to the user-specified service.

8. The AI based method of any one of aspects 1-7, wherein the inventory threshold includes a supply inventory threshold and a medical staff inventory threshold.

9. The AI based method of any one of aspects 1-8, wherein the user device is a telephone, and the matching appointment is conveyed to the user through a verbal communication transmitted through a speaker of the telephone.

10. The AI based method of any one of aspects 1-9, wherein the scheduling database comprises a regulatory guidance database that includes a prioritization schedule corresponding to one or more services.

11. An artificial intelligence (AI) based system for improving patient appointment scheduling and inventory management, the system comprising: a server including one or more processors and a natural language processing (NLP) model that is configured to receive an appointment request from a user, wherein the NLP model is trained with a plurality of verbal responses regarding appointment scheduling of a plurality of users, and the NLP model is configured to output one or more textual transcriptions and one or more intent interpretations corresponding to the one or more textual transcriptions; and one or more memories, storing instructions thereon that, when executed by the one or more processors, cause the one or more processors to: initiate, based on the appointment request, a patient appointment data stream including verbal responses from the user regarding an appointment of the user; apply, while simultaneously receiving the patient appointment data stream, the NLP model to the verbal responses from the user to output (i) textual transcriptions corresponding to the verbal responses from the user and (ii) intent interpretations corresponding to the textual transcriptions; query a scheduling database to determine a matching appointment that satisfies a distance threshold, a date threshold, a service threshold, and an inventory threshold based on the textual transcriptions and the intent interpretations; and cause a user device of the user to convey the matching appointment to the user.

12. The AI based system of aspect 11, wherein the scheduling database stores service location data corresponding to a plurality of service locations, and the instructions, when executed by the one or more processors, further cause the one or more processors to: receive new service location data corresponding to a new service location that includes a new service location address; automatically store the new service location data into the scheduling database; receive a subsequent appointment request from a different user; and query the scheduling database to determine a subsequent matching appointment, wherein the scheduling database includes the new service location data.

13. The AI based system of any one of aspects 11-12, wherein the instructions, when executed by the one or more processors, further cause the one or more processors to: transmit, by utilizing a fulfillment microservice, a query request to a scheduling microservice; and responsive to receiving the query request, query, by utilizing the scheduling microservice, the scheduling database to determine the matching appointment.

14. The AI based system of any one of aspects 11-13, wherein the scheduling database stores service location data corresponding to a plurality of service locations, and the instructions, when executed by the one or more processors, further cause the one or more processors to: determine a location of the user based on the textual transcriptions; convert the location of the user to a coordinate value; convert a respective service location address for each respective service location to a respective coordinate value; calculate a respective service location distance from the location of the user for each respective service location of the plurality of service locations; determine a sorted list of service locations based on the respective service location distance for each respective service location of the plurality of service locations; and select the matching appointment from the sorted list based on a subset of service locations on the sorted list that satisfy the distance threshold, wherein the distance threshold corresponds to a maximum distance value from the location of the user.

15. The AI based system of any one of aspects 11-14, wherein the scheduling database comprises scheduling data corresponding to a plurality of service locations, wherein the scheduling data corresponding to each service location includes a schedule calendar and an inventory listing.

16. The AI based system of aspect 15, wherein the instructions, when executed by the one or more processors, further cause the one or more processors to: compare the schedule calendar and the inventory listing for each respective service location in the plurality of service locations to the date threshold and the inventory threshold; and determine the matching appointment based on a first respective service location that satisfies the distance threshold, the service threshold, the date threshold, and the inventory threshold.

17. A tangible machine-readable medium comprising instructions for improving patient appointment scheduling and inventory management that, when executed, cause a machine to at least: receive an appointment request from a user; initiate, based on the appointment request, a patient appointment data stream including verbal responses from the user regarding an appointment of the user; apply, while simultaneously receiving the patient appointment data stream, a natural language processing (NLP) model to the verbal responses from the user to output (i) textual transcriptions corresponding to the verbal responses from the user and (ii) intent interpretations corresponding to the textual transcriptions, wherein the NLP model is trained with a plurality of verbal responses regarding appointment scheduling of a plurality of users, and the NLP model is configured to output one or more textual transcriptions and one or more intent interpretations corresponding to the one or more textual transcriptions; query a scheduling database to determine a matching appointment that satisfies a distance threshold, a date threshold, a service threshold, and an inventory threshold based on the textual transcriptions and the intent interpretations; and cause a user device of the user to convey the matching appointment to the user.

18. The tangible machine-readable medium of aspect 17, wherein the scheduling database stores service location data corresponding to a plurality of service locations, and the instructions, when executed, further cause the machine to at least: receive new service location data corresponding to a new service location that includes a new service location address; automatically store the new service location data into the scheduling database; receive a subsequent appointment request from a different user; and query the scheduling database to determine a subsequent matching appointment, wherein the scheduling database includes the new service location data.

19. The tangible machine-readable medium of any of aspects 17-18, wherein the instructions, when executed, further cause the machine to at least: transmit, by utilizing a fulfillment microservice, a query request to a scheduling microservice; and responsive to receiving the query request, query, by utilizing the scheduling microservice, the scheduling database to determine the matching appointment.

20. The tangible machine-readable medium of any of aspects 17-19, wherein the scheduling database stores service location data corresponding to a plurality of service locations, and the instructions, when executed, further cause the machine to at least: determine a location of the user based on the textual transcriptions; convert the location of the user to a coordinate value; convert a respective service location address for each respective service location to a respective coordinate value; calculate a respective service location distance from the location of the user for each respective service location of the plurality of service locations; determine a sorted list of service locations based on the respective service location distance for each respective service location of the plurality of service locations; and select the matching appointment from the sorted list based on a subset of service locations on the sorted list that satisfy the distance threshold, wherein the distance threshold corresponds to a maximum distance value from the location of the user.

ADDITIONAL CONSIDERATIONS

The following considerations also apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

It should also be understood that, unless a term is expressly defined in this patent using the sentence "As used herein, the term" "is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for implementing the concepts disclosed herein, through the principles disclosed herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. An artificial intelligence (AI) based method for improving patient appointment scheduling and inventory management, the method comprising:

receiving, at a server including a natural language processing (NLP) model and one or more processors, an appointment request from a user, wherein the NLP model is trained with a plurality of verbal responses regarding appointment scheduling of a plurality of users, and the NLP model is configured to output one or more textual transcriptions and one or more intent interpretations corresponding to the one or more textual transcriptions;

initiating, by the one or more processors and based on the appointment request, a patient appointment data stream including verbal responses from the user regarding an appointment of the user;

applying, by the one or more processors while simultaneously receiving the patient appointment data stream, the NLP model to the verbal responses from the user to output (i) textual transcriptions corresponding to the verbal responses from the user and (ii) intent interpretations corresponding to the textual transcriptions;

querying, by the one or more processors, a scheduling database to determine a matching appointment that satisfies a distance threshold, a date threshold, a service threshold, and an inventory threshold based on the textual transcriptions and the intent interpretations; and causing, by the one or more processors, a user device of the user to convey the matching appointment to the user.

2. The AI based method of claim 1, wherein the scheduling database stores service location data corresponding to a plurality of service locations, and the method further comprises:
receiving, at the server, new service location data corresponding to a new service location that includes a new service location address;
automatically storing, by the server, the new service location data into the scheduling database;
receiving, at the server, a subsequent appointment request from a different user; and
querying, by the one or more processors, the scheduling database to determine a subsequent matching appointment, wherein the scheduling database includes the new service location data.

3. The AI based method of claim 1, wherein querying the scheduling database further comprises:
transmitting, by a fulfillment microservice, a query request to a scheduling microservice; and
responsive to receiving the query request, querying, by the scheduling microservice, the scheduling database to determine the matching appointment.

4. The AI based method of claim 1, wherein the scheduling database stores service location data corresponding to a plurality of service locations, and the method further comprises:
determining, by the one or more processors, a location of the user based on the textual transcriptions;
converting, by the one or more processors, the location of the user to a coordinate value;
converting, by the one or more processors, a respective service location address for each respective service location to a respective coordinate value;
calculating, by the one or more processors, a respective service location distance from the location of the user for each respective service location of the plurality of service locations;
determining, by the one or more processors, a sorted list of service locations based on the respective service location distance for each respective service location of the plurality of service locations; and
selecting, by the one or more processors, the matching appointment from the sorted list based on a subset of service locations on the sorted list that satisfy the distance threshold, wherein the distance threshold corresponds to a maximum distance value from the location of the user.

5. The AI based method of claim 1, wherein the scheduling database comprises scheduling data corresponding to a plurality of service locations, wherein the scheduling data corresponding to each service location includes a schedule calendar and an inventory listing.

6. The AI based method of claim 5, further comprising:
comparing, by the one or more processors, the schedule calendar and the inventory listing for each respective service location in the plurality of service locations to the date threshold and the inventory threshold; and
determining, by the one or more processors, the matching appointment based on a first respective service location that satisfies the distance threshold, the service threshold, the date threshold, and the inventory threshold.

7. The AI based method of claim 1, wherein the textual transcriptions includes a user-specified service, and the service threshold corresponds to the user-specified service.

8. The AI based method of claim 1, wherein the inventory threshold includes a supply inventory threshold and a medical staff inventory threshold.

9. The AI based method of claim 1, wherein the user device is a telephone, and the matching appointment is conveyed to the user through a verbal communication transmitted through a speaker of the telephone.

10. The AI based method of claim 1, wherein the scheduling database comprises a regulatory guidance database that includes a prioritization schedule corresponding to one or more services.

11. An artificial intelligence (AI) based system for improving patient appointment scheduling and inventory management, the system comprising:
a server including one or more processors and a natural language processing (NLP) model that is configured to receive an appointment request from a user, wherein the NLP model is trained with a plurality of verbal responses regarding appointment scheduling of a plurality of users, and the NLP model is configured to output one or more textual transcriptions and one or more intent interpretations corresponding to the one or more textual transcriptions; and
one or more memories, storing instructions thereon that, when executed by the one or more processors, cause the one or more processors to:
initiate, based on the appointment request, a patient appointment data stream including verbal responses from the user regarding an appointment of the user;
apply, while simultaneously receiving the patient appointment data stream, the NLP model to the verbal responses from the user to output (i) textual transcriptions corresponding to the verbal responses from the user and (ii) intent interpretations corresponding to the textual transcriptions;
query a scheduling database to determine a matching appointment that satisfies a distance threshold, a date threshold, a service threshold, and an inventory threshold based on the textual transcriptions and the intent interpretations; and
cause a user device of the user to convey the matching appointment to the user.

12. The AI based system of claim 11, wherein the scheduling database stores service location data corresponding to a plurality of service locations, and the instructions, when executed by the one or more processors, further cause the one or more processors to:
receive new service location data corresponding to a new service location that includes a new service location address;
automatically store the new service location data into the scheduling database;
receive a subsequent appointment request from a different user; and
query the scheduling database to determine a subsequent matching appointment, wherein the scheduling database includes the new service location data.

13. The AI based system of claim 11, wherein the instructions, when executed by the one or more processors, further cause the one or more processors to:
transmit, by utilizing a fulfillment microservice, a query request to a scheduling microservice; and
responsive to receiving the query request, query, by utilizing the scheduling microservice, the scheduling database to determine the matching appointment.

14. The AI based system of claim 11, wherein the scheduling database stores service location data corresponding to a plurality of service locations, and the instructions, when executed by the one or more processors, further cause the one or more processors to:
- determine a location of the user based on the textual transcriptions;
- convert the location of the user to a coordinate value;
- convert a respective service location address for each respective service location to a respective coordinate value;
- calculate a respective service location distance from the location of the user for each respective service location of the plurality of service locations;
- determine a sorted list of service locations based on the respective service location distance for each respective service location of the plurality of service locations; and
- select the matching appointment from the sorted list based on a subset of service locations on the sorted list that satisfy the distance threshold, wherein the distance threshold corresponds to a maximum distance value from the location of the user.

15. The AI based system of claim 11, wherein the scheduling database comprises scheduling data corresponding to a plurality of service locations, wherein the scheduling data corresponding to each service location includes a schedule calendar and an inventory listing.

16. The AI based system of claim 15, wherein the instructions, when executed by the one or more processors, further cause the one or more processors to:
- compare the schedule calendar and the inventory listing for each respective service location in the plurality of service locations to the date threshold and the inventory threshold; and
- determine the matching appointment based on a first respective service location that satisfies the distance threshold, the service threshold, the date threshold, and the inventory threshold.

17. A tangible machine-readable medium comprising instructions for improving patient appointment scheduling and inventory management that, when executed, cause a machine to at least:
- receive an appointment request from a user;
- initiate, based on the appointment request, a patient appointment data stream including verbal responses from the user regarding an appointment of the user;
- apply, while simultaneously receiving the patient appointment data stream, a natural language processing (NLP) model to the verbal responses from the user to output (i) textual transcriptions corresponding to the verbal responses from the user and (ii) intent interpretations corresponding to the textual transcriptions, wherein the NLP model is trained with a plurality of verbal responses regarding appointment scheduling of a plurality of users, and the NLP model is configured to output one or more textual transcriptions and one or more intent interpretations corresponding to the one or more textual transcriptions;
- query a scheduling database to determine a matching appointment that satisfies a distance threshold, a date threshold, a service threshold, and an inventory threshold based on the textual transcriptions and the intent interpretations; and
- cause a user device of the user to convey the matching appointment to the user.

18. The tangible machine-readable medium of claim 17, wherein the scheduling database stores service location data corresponding to a plurality of service locations, and the instructions, when executed, further cause the machine to at least:
- receive new service location data corresponding to a new service location that includes a new service location address;
- automatically store the new service location data into the scheduling database;
- receive a subsequent appointment request from a different user; and
- query the scheduling database to determine a subsequent matching appointment, wherein the scheduling database includes the new service location data.

19. The tangible machine-readable medium of claim 17, wherein the instructions, when executed, further cause the machine to at least:
- transmit, by utilizing a fulfillment microservice, a query request to a scheduling microservice; and
- responsive to receiving the query request, query, by utilizing the scheduling microservice, the scheduling database to determine the matching appointment.

20. The tangible machine-readable medium of claim 17, wherein the scheduling database stores service location data corresponding to a plurality of service locations, and the instructions, when executed, further cause the machine to at least:
- determine a location of the user based on the textual transcriptions;
- convert the location of the user to a coordinate value;
- convert a respective service location address for each respective service location to a respective coordinate value;
- calculate a respective service location distance from the location of the user for each respective service location of the plurality of service locations;
- determine a sorted list of service locations based on the respective service location distance for each respective service location of the plurality of service locations; and
- select the matching appointment from the sorted list based on a subset of service locations on the sorted list that satisfy the distance threshold, wherein the distance threshold corresponds to a maximum distance value from the location of the user.

* * * * *